(12) United States Patent
Delabie

(10) Patent No.: US 9,017,291 B2
(45) Date of Patent: Apr. 28, 2015

(54) LUER CONNECTOR

(75) Inventor: Patrice Delabie, Cold Spring, NY (US)

(73) Assignee: Becton Dickinson France, Le Pont de Claix (FR)

( * ) Notice: Subject to any disclaimer, the term of this patent is extended or adjusted under 35 U.S.C. 154(b) by 68 days.

(21) Appl. No.: 13/379,235

(22) PCT Filed: Jun. 24, 2009

(86) PCT No.: PCT/IB2009/006577
§ 371 (c)(1),
(2), (4) Date: Mar. 13, 2012

(87) PCT Pub. No.: WO2010/150042
PCT Pub. Date: Dec. 29, 2010

(65) Prior Publication Data
US 2012/0179108 A1 Jul. 12, 2012

(51) Int. Cl.
*A61M 5/31* (2006.01)
*A61M 5/34* (2006.01)

(52) U.S. Cl.
CPC ............ *A61M 5/347* (2013.01); *A61M 5/3134* (2013.01); *A61M 5/344* (2013.01)

(58) Field of Classification Search
CPC ..... A61M 5/3134; A61M 5/34; A61M 5/344; A61M 5/345; A61M 5/346
USPC ........................................................ 604/187
See application file for complete search history.

(56) References Cited

U.S. PATENT DOCUMENTS

| | | | |
|---|---|---|---|
| 4,589,871 A * | 5/1986 | Imbert | 604/240 |
| 4,676,530 A | 6/1987 | Nordgren et al. | |
| 5,071,413 A * | 12/1991 | Utterberg | 604/533 |
| 5,702,374 A * | 12/1997 | Johnson | 604/533 |
| 6,027,482 A * | 2/2000 | Imbert | 604/256 |
| 6,280,418 B1 | 8/2001 | Reinhard et al. | |
| 6,969,375 B2 | 11/2005 | Thibault et al. | |

FOREIGN PATENT DOCUMENTS

| | | |
|---|---|---|
| EP | 0716860 A2 | 6/1996 |
| EP | 1563863 A1 | 8/2005 |
| FR | 2809316 A1 | 11/2001 |
| WO | 0191839 A1 | 12/2001 |
| WO | 2006087763 A1 | 8/2006 |
| WO | WO 2006087763 A1 * | 8/2006 |

* cited by examiner

*Primary Examiner* — Laura Bouchelle
(74) *Attorney, Agent, or Firm* — The Webb Law Firm

(57) ABSTRACT

The invention relates to a drug delivery device comprising a container for a product, said container comprising a distal tip having a longitudinal axis A and a channel providing a passageway for the transfer of said product, the outer surface of said distal tip comprising a proximal portion and a distal portion linked to each other by a coupling portion, said proximal portion, distal portion and coupling portion being aligned on said longitudinal axis A, wherein the greatest external diameter of said coupling portion is greater than the greatest external diameter of said distal portion on a length L measured along said longitudinal axis A at least equal to 1 mm. The invention also relates to an assembly comprising such a drug delivery device and an adaptor.

11 Claims, 4 Drawing Sheets

LUER CONNECTOR

Figure 1:
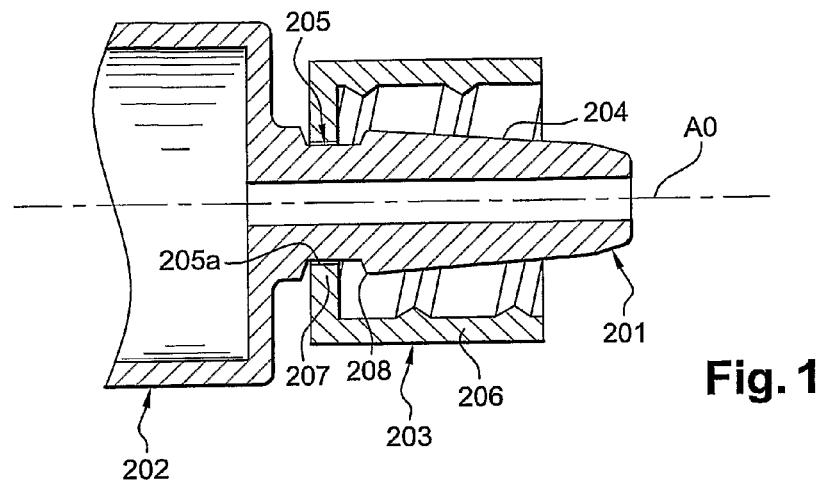

The present invention relates to a drug delivery device having a specific distal tip and to an assembly comprising said drug delivery device and an adaptor, such as a Luer lock adaptor, allowing a safe connection of the adaptor on the drug delivery device, in view of further connecting a connector element, such as for example an IV (Intra Venous) connector, an IM (Intra Muscular) connector, a subcutaneous connector, to said drug delivery device.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, and the "proximal direction" is to be understood as meaning the opposite direction to the direction of injection.

Various medical devices are known for transferring and/or storing medical fluids, such as syringes, perfusion and transfusion devices and connectors. It is essential for safety reasons that these various medical devices can be assembled together correctly and securely.

A conventional drug delivery device usually comprises a hollow body forming a container for a medical product : the distal end of the body forming the container usually comprises a tip in which an axial passageway is arranged, through which the said product is ejected from the container.

The handling of liquid products, in particular for a parenteral administration to a patient which is carried out via a perfusion device, as often in hospitals or in emergency situations, implies, in a general manner, the use of connectors. Such connectors make it possible to seal assemblies of medical devices and provide protection against the contamination of the medical liquid products that they contain.

The connectors, like for example IV connectors, are usually connected to the drug delivery device by means of intermediate elements such as adaptors. Usually, these adaptors are first mounted on the distal tip of the drug delivery device: the connector, such as an IV connector, is then mounted on the free end of the adaptor, for example by screwing. In such a step, the adaptor is friction forced on the distal tip of the drug delivery device and is supposed to remain immobile, thanks to friction forces, with respect to the distal tip while the connector is screwed on the adaptor. Usually, a shoulder is present on the distal tip to prevent the adaptor to slide distally with respect to the distal tip.

EP 0 716 860 A2 describes at its FIG. 10 such a distal tip comprising a shoulder aiming at preventing the adaptor to slide distally once said adaptor is mounted on said distal tip.

Distal tips, provided with a groove in which part of the adaptor gets stuck once it is friction forced on the distal tip, have also been proposed: WO01/91839 describes such distal tips. Such a distal tip of the prior art, together with an adaptor mounted thereon, is shown on FIG. 1.

On this figure is shown a distal tip 201 of a drug delivery device 202 of the prior art having a longitudinal axis A0, on which an adaptor 203 is mounted. The distal tip 201 comprises a tapered outer surface 204 provided with a groove 205 having a flat bottom 205a. The adaptor 203 comprises a ring 206 and an annular ridge 207. The annular ridge 207 of the adaptor 203 is radially expandable upon forces exerted on its inner wall. The adaptor 203 is friction forced on the distal tip 201. Thanks to its capability to deform, the annular ridge 207 expands when it is friction forced on the tapered outer surface 204 of the distal tip 201, until it gets stuck in the groove 205, as shown on FIG. 1. In the position shown on this figure, the adaptor 203 is supposed to be immobile with respect to the distal tip 201 thanks to friction forces present between the annular ridge 207 and the surface of the flat bottom 205a of the groove 205. Moreover, the adaptor 203 is prevented from sliding distally with respect to the distal tip 201 thanks to the step 208 formed at the junction of the groove 205 with the distal portion of the outer surface 204 of the distal tip 201.

However, problems have been reported concerning the use of some adaptors with various drug delivery devices: actually, most of the adaptors that are available for use in the medical field for the purpose of connecting drug delivery devices with connectors are made of plastic material. The capability of deformation of such plastic material is influenced by aging and temperature conditions. As a result, it may happen that, for example after a certain time or after having been submitted to specific conditions like sterilization temperatures, the adaptor 203 does not remain immobile with respect to the distal tip 201. In particular, it may happen that the friction forces are not important enough to prevent the adaptor 203 to rotate, although with friction, with respect to the distal tip 201 when the user tries to screw a connector on to the adaptor 203: it is therefore impossible for the user to determine whether the connector is well fitted in the adaptor or not and, as a consequence, whether the connector is well connected to the distal tip of the drug delivery device. An incorrect connection between the drug delivery device and the connector may cause the displacement of the adaptor and/or of the connector in regards to the drug delivery device, that could lead to leaks of product and therefore incorrect doses administered to the patient and product waste.

Moreover, the distal tips of the prior art such as the one shown on FIG. 1 have the drawback that they are rendered more frangible by the presence of the groove, the wall of the tip, at the location of the groove, being thinner: this drawback constitutes a serious problem when the distal tips are made of glass. Such distal tips may break during use.

There is therefore a need for a drug delivery device with a specific distal tip that would allow the reproducible connection between said drug delivery device and an adaptor, and that would be resistant to potential breakage, especially when said distal tip is made of glass.

One aspect of the present invention is a drug delivery device comprising a container for a product, said container comprising a distal tip having a longitudinal axis A and a channel defined through said distal tip, said channel providing a passageway for the transfer of said product, said distal tip comprising at least a distal portion, and a coupling portion located proximally from said distal portion, characterized in that the greatest external diameter of said coupling portion is greater than the greatest external diameter of said distal portion on a length L measured along said longitudinal axis A at least equal to 1 mm.

Because of its specific dimensions, the distal tip of the drug delivery device of the invention allows the secure and reproducible fixation of an adaptor on its outer surface. Moreover, when it is made of glass, the distal tip of the drug delivery device of the invention is particularly resistant to potential breakage during its handling by a user.

As will appear from the description below, such a specific length L allows an adaptor to be in tight contact and/or friction contact with the distal tip on a surface sufficient for preventing the adaptor to rotate and/or translate with respect to the distal tip. Moreover, when the distal tip is made of glass, the substantial length L prevents the formation of cracks during the manufacture of said distal tip, when the glass is heated before being shaped in its final form. As a consequence, such a substantial length L allows the distal tip to be more resistant to potential breakage.

In an embodiment of the invention, the drug delivery device comprises a proximal portion located proximally from said coupling portion, the proximal external diameter of said coupling portion being greater than the distal external diameter of said proximal portion, thereby, defining a step at the junction of said coupling portion with said proximal portion: such a step is intended to cooperate with a specific bump provided on the adaptor in order to prevent the distal movement of the adaptor with respect to the distal tip, once the adaptor is fitted on the distal tip.

In an embodiment of the invention, the length L is at least equal to 2 mm. Such a substantial length enables to avoid sharp angles and therefore potential cracks formation on the distal tip during the manufacture of said distal tip. Moreover, part of the adaptor is therefore in contact, and in particular in friction contact, with a substantial surface of the distal tip when it is fitted on the distal tip.

In an embodiment of the invention, the coupling portion comprises at least a cylindrical portion. By cylindrical portion is meant in the present application a portion having a substantial length measured along the longitudinal axis A, such as a band, and not a point-shaped rib. As will appear from the description below, such a cylindrical portion allows an adaptor to be in tight contact and/or friction contact with the distal tip on a surface sufficient for preventing the adaptor to rotate with respect to the distal tip.

In an embodiment of the invention, at least part of an outer surface of said coupling portion comprises a rough portion. This rough portion may be obtained by a coating containing a roughening agent such as ceramic particles. This rough portion may also be obtained by the use of a specific forming tool having a specific roughness and/or shape.

Such a roughening agent and/or specific forming tool create reliefs on the outer surface of the coupling portion, where the distal tip is in contact with the adaptor, thereby improving the friction force between the adaptor and the distal tip. Such a rough portion therefore increases the force that is necessary in order to remove the adaptor from the distal tip and the adaptor is prevented from rotating and translating with respect to the distal tip around the longitudinal axis A.

In an embodiment of the invention, an outer surface of the coupling portion is provided with an annular rib: such an annular rib increases, on a localized circumference of the coupling portion, the external diameter of the coupling portion. It therefore increases the force that is necessary to remove the adaptor and prevents thereby the rotation and translation of said adaptor. In an embodiment of the invention, this annular rib is made of glass. Preferably also, the distal tip is made of glass.

Another aspect of the present invention is an assembly comprising a drug delivery device as described above and an adaptor intended to be fitted on the distal tip of said drug delivery device, said adaptor comprising a ring provided with at least one inner projection, said inner projection being capable of cooperating with an outer surface of the coupling portion of said drug delivery device, when said adaptor is fitted on said distal tip, so as to prevent rotational and translational movement of said adaptor with respect to said distal tip, around said longitudinal axis A. In particular, the inner projection cooperates with the outer surface of the coupling portion by friction contact with said outer surface.

In an embodiment of the invention, said ring is radially and outwardly expandable from a rest position, in which said one inner projection defines a first internal diameter Dr of said ring, and a stressed position, in which said one inner projection defines a second internal diameter Ds of said ring, Ds being greater than Dr, said ring being in its stressed position when said at least one inner projection cooperates with the outer surface of said coupling portion, so as to prevent rotational and translational movement of said adaptor with respect to said distal tip.

In an embodiment of the invention, Dr ranges from 90% to 97% of the external diameter of the outer surface of said coupling portion. This allows in particular the adaptor to keep its deformation capabilities, even once it has been deformed in order to be friction forced the adaptor on the distal tip.

In an embodiment of the invention, said at least one inner projection is provided on its inner surface with at least one bump, said bump being intended to cooperate with the step of the distal tip as seen above so as to prevent distal movement of the adaptor when said adaptor is fitted on said distal tip. In particular, said bump cooperates with said step by becoming engaged therein, thereby increasing the force necessary to move the adaptor distally with respect to the distal tip.

In an embodiment of the invention, said distal tip is made of glass and said adaptor is made of a plastic material preferably chosen to have a heat deflection temperature (DTUL) higher than 125° C. per ASTM D648 standard: such plastic material keep their deformation capabilities even after a sterilization step at high temperature. For example, the plastic material is a polycarbonate HT "High temperature".

Figure 2A:
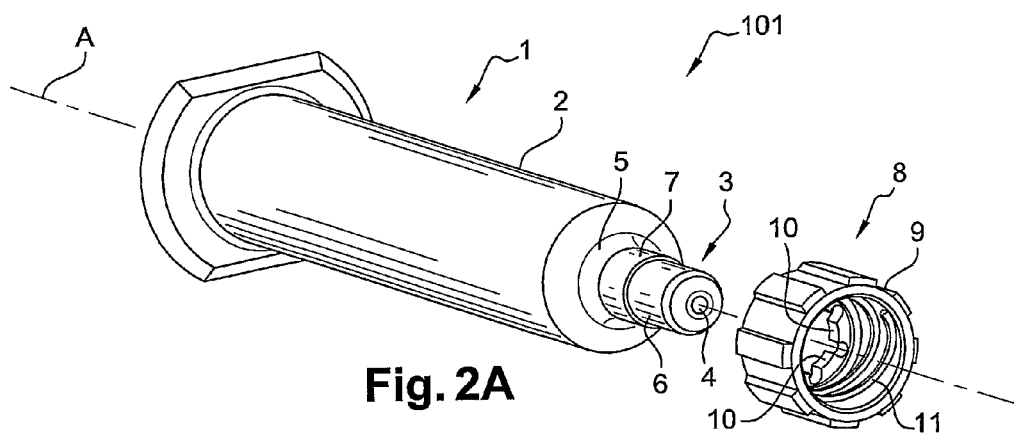
Figure 2B:
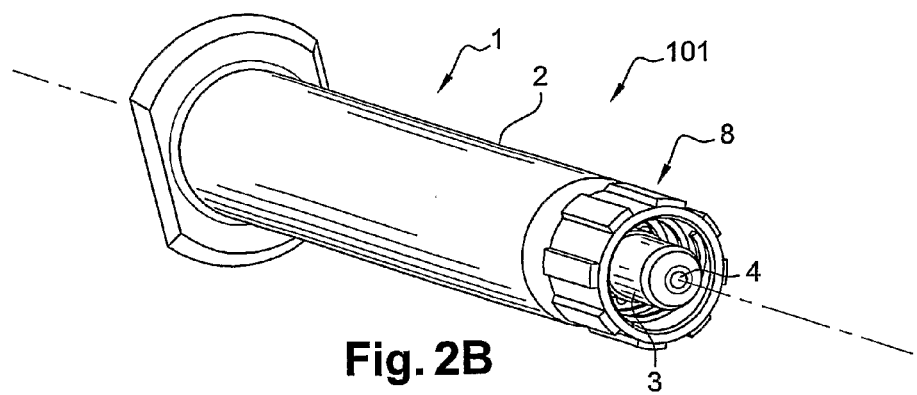
Figure 3A:
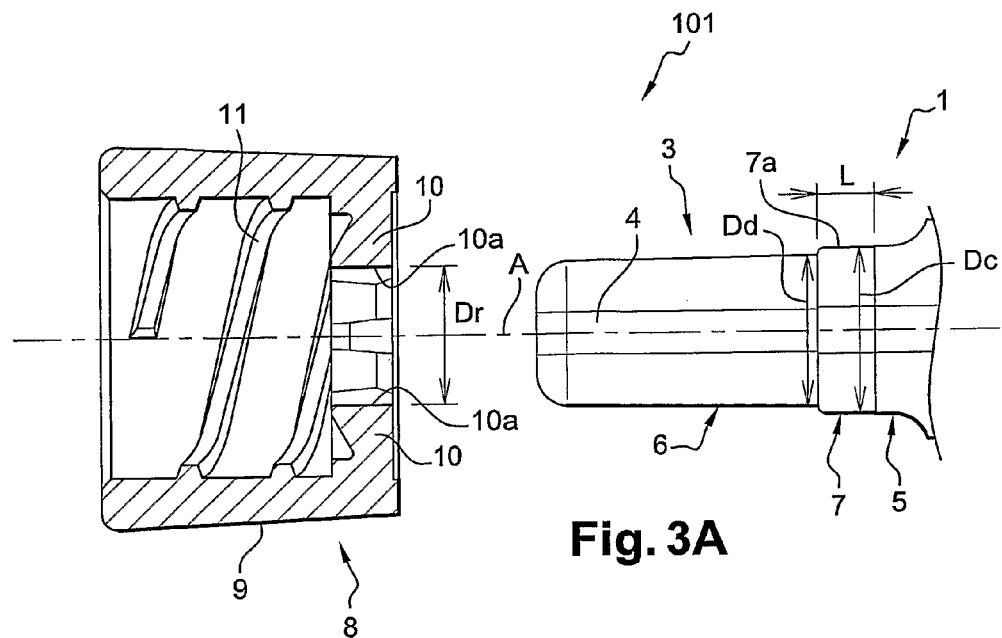
Figure 3B:
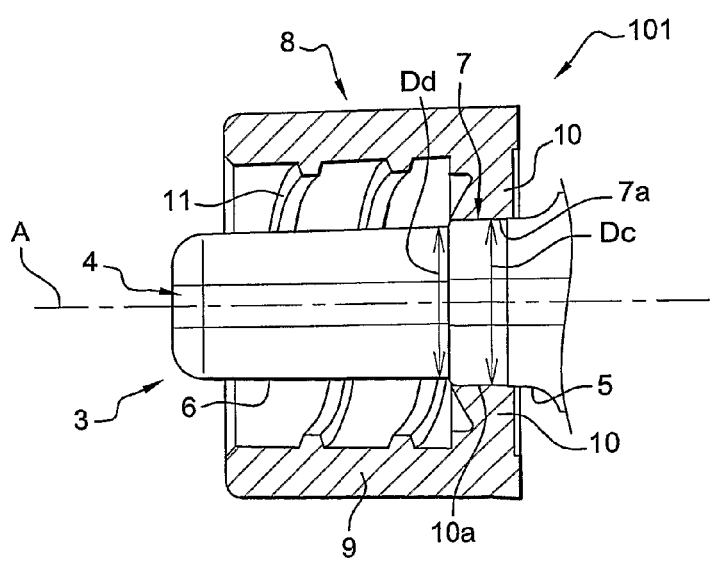
Figure 4:
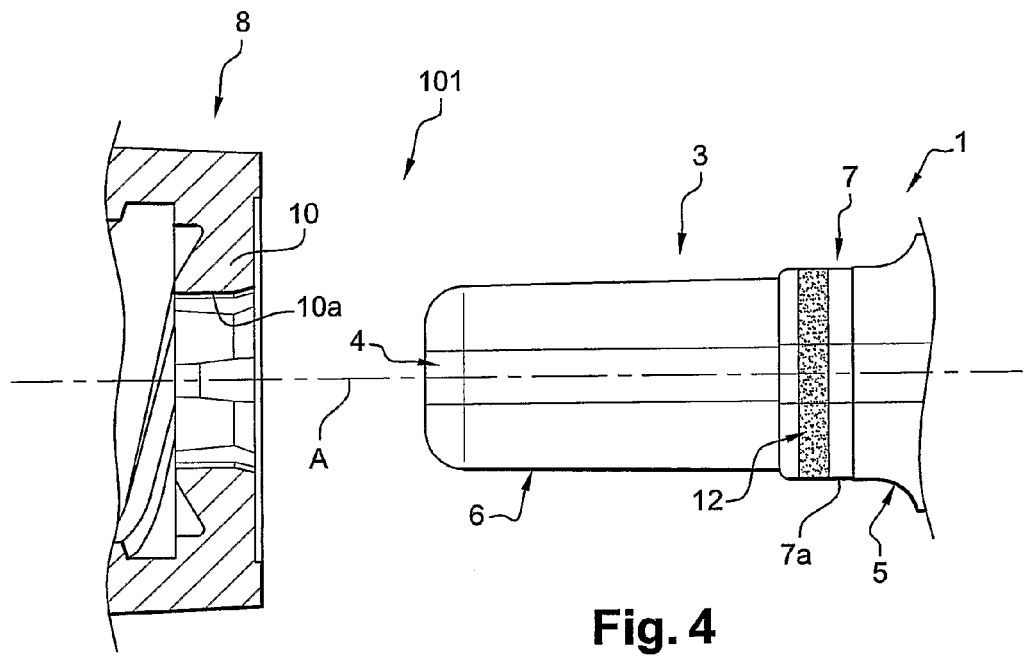
Figure 5:
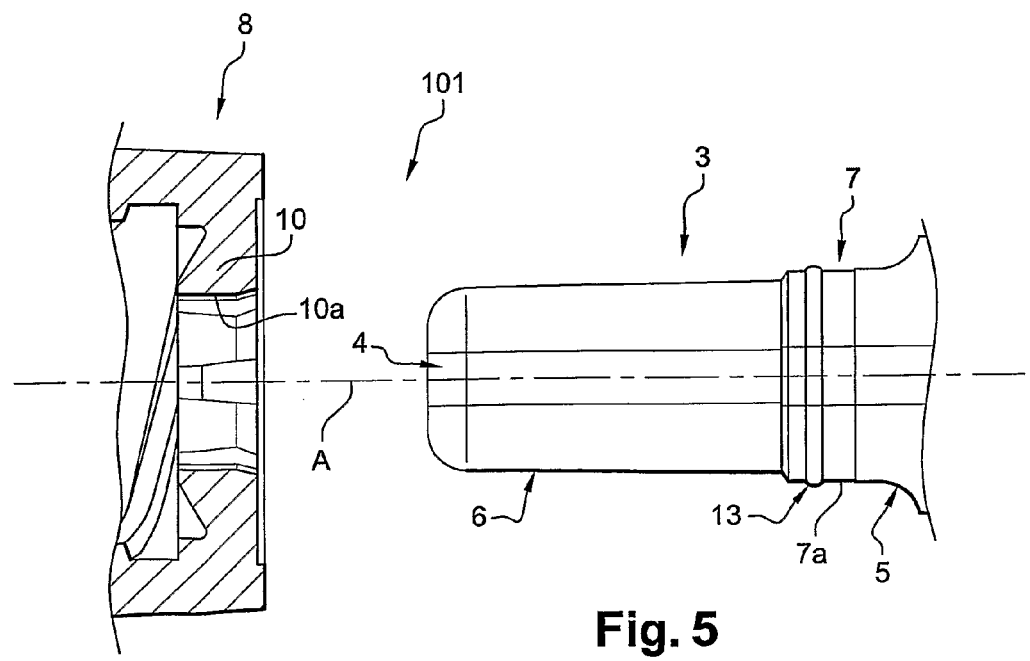
Figure 6A:
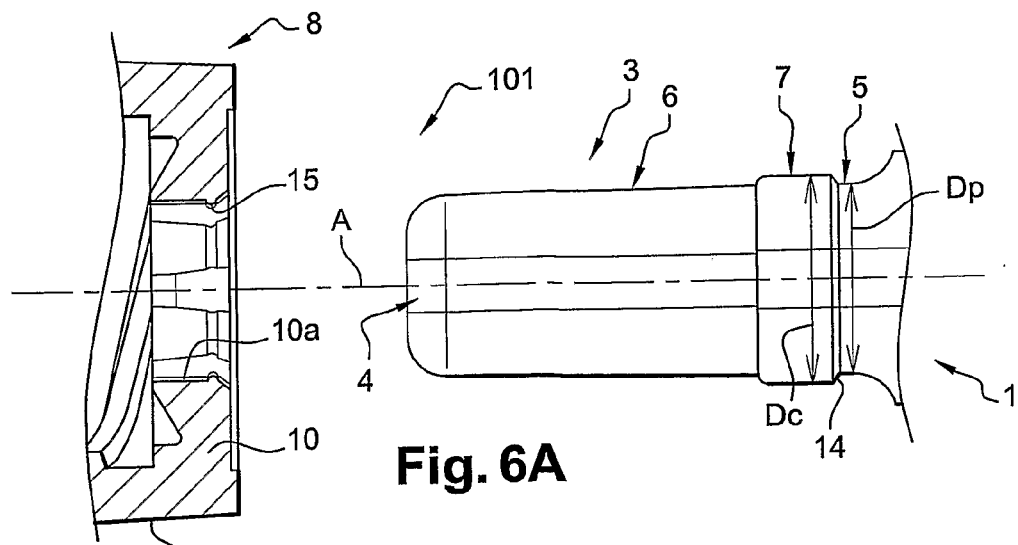
Figure 6B:
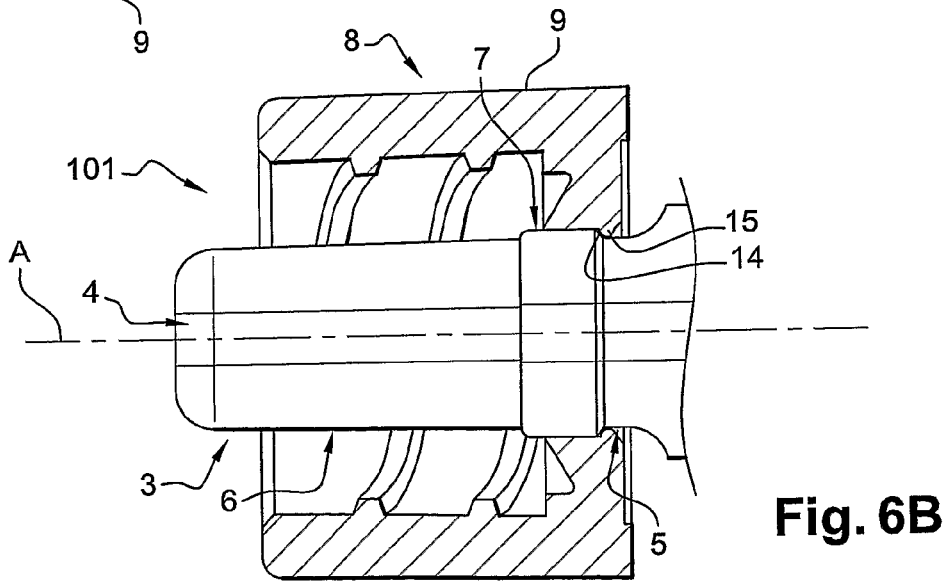
Figure 7:
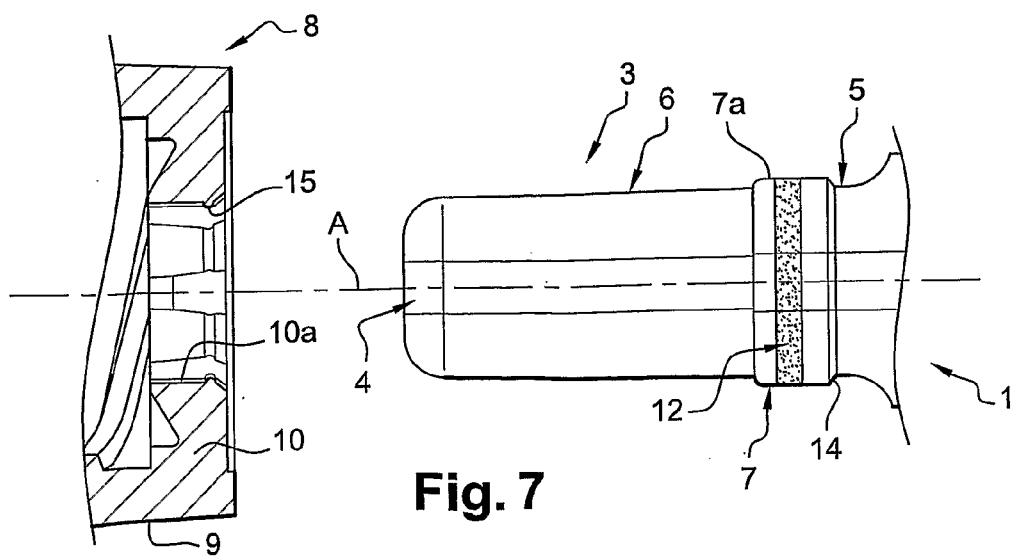

The invention and the advantages that arise therefrom will clearly emerge from the detailed description that is given below with reference to the appended drawings in which:

FIG. 1 is a cross section view of a drug delivery device of the prior art with an adaptor mounted on the distal tip of the drug delivery device, FIGS. 2A and 2B are perspective views of a first embodiment of an assembly of the invention respectively before mounting the adaptor on the drug delivery device and once the adaptor is mounted on the distal tip of the drug delivery device, FIGS. 3A and 3B are partial cross section views of the drug delivery device and assembly of FIGS. 2A and 2B respectively, FIG. 4 is a partial cross section view of a second embodiment of the drug delivery device and of the assembly of the invention, FIG. 5 is a partial cross section view of a third embodiment of the drug delivery device and of the assembly of the invention, FIGS. 6A and 6B are partial cross section views of a fourth embodiment of the drug delivery device and of the assembly of the invention, before and after the adaptor is fitted on the distal tip, FIG. 7 is a partial cross section view of a fifth embodiment of the drug delivery device and of the assembly of the invention.

With reference to FIG. 2A is shown an assembly 101 of the invention comprising a drug delivery device 1 of the invention comprising a container 2 having a distal tip 3 with a longitudinal axis A. On the example shown, the container 2 and the distal tip 3 are made of one single element. The container 2 has a tubular shape and defines a reservoir for a product, for example a medical fluid. The container 2 and the distal tip 3 are preferably made of glass material. The container 2 may be sealed at its proximal end by a piston (not shown). The distal tip 3 encompasses a channel 4 aligned with the longitudinal axis A and providing a passageway for the transfer of the product, either from the container 2 to a connector (not shown) such as for example an IV (Intra Venous) connector, an IM (Intra Muscular) connector, a subcutaneous connector, or others. On the example shown, the outer surface of the distal tip 3 comprises a proximal portion 5, a distal portion 6 and a coupling portion 7, all aligned along longitudinal axis A. In this example, the proximal portion 5 and distal portion 6 have a frusto conical shape and the coupling portion 7 is cylindrical.

With reference to FIG. 3A, the external diameter (Dc on FIG. 3A) of the coupling portion 7 is greater than the greatest external diameter (Dd on FIG. 3A) of the frusto-conical distal portion 6 of the outer surface of the distal tip 3. On the embodiment shown on this figure, the external diameter Dc of the coupling portion 7 is equal or inferior to the smallest external diameter of the frusto-conical proximal portion 5. As appears from FIGS. 2A and 3A, the coupling portion 7 has a substantial length L along the longitudinal axis A. For example, such a length L measured along the longitudinal axis A may range from 10% to 40% of the length of the distal portion 6. For example, if the length of the distal portion 6 is 8 mm, then the length of the coupling portion 7 may range from 1 to 3 mm. The length L is at least 1 mm. Such a length allows defining a substantial surface on said coupling portion 7, for receiving part of the adaptor intended to be mounted on the distal tip 3. Moreover, when the distal tip is made of glass, such a length enables to avoid sharp angles and formation of cracks during the manufacture of the distal tip, at the time the glass is heated in order to be shaped. The resulting distal tip is therefore more resistant to potential breakage.

On FIG. 2A is also shown an adaptor 8 of the assembly 101 of the invention, intended to be fitted on the distal tip 3 in order to further connect a connector (not shown), such as an IV connector to the drug delivery device 1. The adaptor 8 comprises a ring 9. On the example shown the ring 9 is provided in its proximal region with an inner projection under the form of a discontinuous annular bulge 10 extending radially inwardly. In an example not shown, the inner projection may be a continuous bulge. On the example shown, the inner wall of the ring 9 is provided with an internal thread 11 distally spaced from the discontinuous annular bulge 10.

As will appear later in the following description, in a first step, the adaptor 8 is fitted on the distal tip 3 (see FIGS. 2B and 3B), and then, in a second step, a connector (not shown), such as an IV connector, is intended to be screwed on the adaptor 8, on the internal thread 11 of said adaptor 8, in order to connect safely the drug delivery device 1 to the said connector so as to realize the transfer of the product from the drug delivery device 1 to the connector or vice-versa. The said connector is provided with an external thread intended to cooperate with the internal thread 11 of the adaptor 8 in order to screw the adaptor 8 on the connector. On FIG. 3B is shown the assembly 101 of FIG. 2B, once the adaptor 8 has been friction forced on the distal tip 3. In reference with FIG. 3B, it appears clearly that, when the adaptor 8 is fitted on the distal tip 3, the inner surface 10a of the discontinuous annular bulge 10 comes in tight contact with the outer surface 7a of the coupling portion 7. This tight contact or friction contact between the outer surface 7a of the coupling portion 7 and the inner surface 10a of the discontinuous annular bulge 10 prevents the rotational and translational movement of the adaptor 8 with respect to the distal tip 3 around the longitudinal axis A.

With reference to FIGS. 3A and 3B, the adaptor 8 is generally made in a material flexible enough to allow said adaptor 8 to adopt a rest position, shown on FIG. 3A, in which the discontinuous bulge 10 defines a first internal diameter Dr, and a stressed position, shown on FIG. 3B, in which the discontinuous bulge 10 defines a second internal diameter Ds, Ds being greater than Dr. The ring 9 is therefore radially and outwardly expandable upon a stress exerted on the inner surface 10a of the bulge 10 in the outward and radial direction. As shown on FIG. 3B, such a stress is exerted on the bulge 10 by the outer surface 7a of the coupling portion 7 of the distal tip 3 when the adaptor 8 is friction forced on the distal tip 3. Actually, when the adaptor 8 is fitted on the distal tip 3 as shown on FIG. 3B, Ds is equal to Dc. For example, the ring 9 is made of plastic material. The adaptor may be made of a plastic material having a heat deflection temperature (DTUL) higher than 125° C. per ASTM D648 standard; such plastic material resists sterilization at high temperature. For example, such a plastic material is a polycarbonate HT "High temperature".

The operation of mounting and fitting an adaptor 8 on a drug delivery device 1 of the assembly 101 of the invention in view of further safely connecting a connector on said drug delivery device will now be described with reference to FIGS. 3A and 3B.

The user is provided with a drug delivery device 1 and an adaptor 8 as shown on FIGS. 2A and 3A. The adaptor 8 is in its rest position as shown on FIG. 3A. The user grasps the drug delivery device 1 with one hand and the adaptor 8 with the other hand. He forces the proximal end of the ring 9 on the distal end of the distal tip 3. The tapered outer surface of the frusto-conical distal portion 6 of the distal tip 3 exerts a radial and outward force on the discontinuous bulge 10 of the adaptor 8, and the ring 9 deforms and expands radially, until it reaches the outer surface 7a of the coupling portion 7 of the distal tip 3, as shown on FIG. 3B. In this stressed position of the adaptor 8, the adaptor 8 is in high friction contact with the distal tip 3 by means of the inner surface 10a of the discontinuous annular bulge 10 being in high friction contact with the outer surface 7a of the coupling portion 7 on a substantial surface. The rotational and translational movement of the adaptor 8 with respect to the distal tip 3 around and along the longitudinal axis A is therefore prevented.

Preferably, Dr ranges from 90% to 98% of Dc. This allows the adaptor 8, and in particular the ring 9, not to lose its deformation capabilities when it is under stress in the position where the adaptor 8 is fitted on the distal tip 3 as shown on FIG. 3B.

For example, the diameter Dc is 4.80 mm, and the internal diameter Dr of the ring 9 defined by the discontinuous bulge 10 in the rest position of the adaptor is 4.54 mm. The greatest external diameter Dd of the frusto-conical distal portion 6 may be for example 4.42 mm.

As a consequence, when the user wishes to proceed to the further step of connecting to the adaptor 8 a connector, such as an IV connector, he just has to grasp the adaptor 8 fitted on the distal tip 3 as shown on FIG. 2B or 3B in one hand and then to screw the connector on to the internal thread 11 of the adaptor 8, without fearing that the adaptor 8 may detach from the distal tip 3. When the external thread of the connector (not shown) is firmly screwed on the internal thread 11 of the adaptor 8, then the user knows that the drug delivery device 1 and the connector are tightly connected without any risk of leakage of the product to be transferred from one piece to the other.

The assembly of the invention therefore allows connecting safely a drug delivery device to a connector without having to fear the adaptor may detach from the drug delivery device.

The assembly of the invention renders the connection of a drug delivery device to a connector, such as an IV connector, particularly simple, safe and reproducible.

On FIGS. 4 and 5 are shown alternative embodiments of the drug delivery device 1 of the invention of FIGS. 2A to 3B. The references designating the same elements as in FIGS. 2A to 3B have been maintained.

On FIG. 4 is shown partially a drug delivery device 1 of the invention with a distal tip 3 such as the one shown on FIG. 3A, wherein the outer surface 7a of the coupling portion 7 is partially coated with a roughening agent, under the form of an annular band 12 of ceramic particles in the example shown. Alternatively, the rough portion can also be obtained by a specific roughness and/or shape of the forming tool during the glass forming operation. Preferably, the annular band 12 of roughening agent does not cover the totality of the outer surface 7a of the coupling portion 7. This allows preserving the mechanical resistance of the distal tip 3, especially when this distal tip 3 is made of glass. The presence of the roughening agent on part of the outer surface 7a of the coupling portion 7 increases the friction forces between the inner surface 10a of the discontinuous annular bulge 10 of the adaptor 8 and the outer surface 7a of the coupling portion 7, when the adaptor 8 is fitted on the distal tip 3. The adaptor 8 is therefore securely prevented from rotating or translating with respect to the distal tip 3 around the longitudinal axis A, even after aging or after having been submitted to high temperatures such as sterilization temperature.

On FIG. 5 is shown partially a drug delivery device with a distal tip 3 such as the one shown on FIG. 3A, wherein the outer surface 7a of the coupling portion 7 is further provided with an annular rib 13: in the example shown, the distal tip 3 and the annular rib 13 are one single element made of glass. In another embodiment not shown, the annular rib could be under the shape of an additional element provided on the outer surface 7a of the coupling portion 7; such an annular rib 13 increases, on a localized circumference of the coupling portion 7, the external diameter of said coupling portion 7 and thus provides for an additional resistance to removal of the adaptor 8 when it is fitted on the distal tip 3.

On FIGS. 6A, 6B and 7 are shown alternative embodiments of the drug delivery device 1 of the invention of FIGS. 2A to 3B, in which the external diameter Dc of the coupling portion 7 is strictly greater than the distal external diameter Dp of the frusto-conical proximal portion 5. The references designating the same elements as in FIGS. 2A to 3B have been maintained.

On FIG. 6A is shown partially a drug delivery device with a distal tip 3 such as the one shown on FIG. 3A, wherein the distal diameter Dp of the frusto-conical proximal portion 5 is strictly less than the external diameter Dc of the coupling portion 7. As a consequence, a step 14 is formed at the junction of the coupling portion 7 with the proximal frusto-conical portion 5.

As appears also from FIG. 6A, the inner projection or discontinuous bulge 10 is provided on its inner surface 10a with a bump 15. As can be seen on FIG. 6B, when the adaptor 8 is fitted on the distal tip 3, the bump 15 cooperates with the step 14 so as to become engaged therein. The engagement of the bump 15 in the step 14 provides additional resistance to removal of the adaptor 8 in the distal direction and prevents distal movement of the adaptor 8 with respect to the distal tip 3.

On FIG. 7 is shown an alternative embodiment of the assembly of FIGS. 6A and 6B, wherein the outer surface 7a of the coupling portion 7 is partially coated with an annular band 12 of ceramic particles or any other roughening agent.

In another embodiment not shown, the coupling portion comprises a frusto conical portion which has a greatest external diameter greater than the greatest external diameter of the distal portion. In such an example, the smallest external diameter of the frusto conical portion of the coupling portion can be smaller or greater than the greatest external diameter of the distal portion.

The assembly of the invention therefore allows connecting safely a drug delivery device to a connector without having to fear the adaptor may detach from the drug delivery device. In addition, by providing added substance material without creating sharp angles, it increases the mechanical strength of the distal tip 3 especially when said distal tip 3 is made of glass material.

The invention claimed is:

1. An assembly comprising:
a drug delivery device comprising: a container for a product, comprising: a distal tip having a longitudinal axis A and a channel defined through said distal tip, said channel providing a passageway for the transfer of said product, said distal tip comprising at least a distal portion having a frusto-conical shape and a distinct coupling portion having a cylindrical shape located proximally from said distal portion, wherein the greatest external diameter of said coupling portion is greater than the greatest external diameter of said distal portion on a length L measured along said longitudinal axis A at least equal to 1 mm, and
an adaptor for receipt on the distal tip of said drug delivery device, said adaptor comprising a ring provided with at least one inner projection having a longitudinal inner surface, said longitudinal inner surface of said inner projection being capable of cooperating with a longitudinal outer surface of the coupling portion of said drug delivery device, when said adaptor is received on said distal tip, so as to prevent rotational and translational movement of said adaptor with respect to said distal tip, around and along said longitudinal axis A.

2. The assembly according to claim 1, wherein the drug delivery device further comprises a proximal portion located proximally from said coupling portion, wherein a proximal external diameter of said coupling portion is greater than a distal external diameter of said proximal portion, thereby defining a step at a junction of said coupling portion with said proximal portion.

3. The assembly according to claim 1, wherein said length L is at least equal to 2 mm.

4. The assembly according to claim 1, wherein said coupling portion comprises at least a cylindrical portion.

5. The assembly according to claim 1, wherein at least part of said longitudinal outer surface of said coupling portion comprises a rough portion.

6. The assembly according to claim 1, wherein said longitudinal outer surface of said coupling portion comprises an annular rib.

7. The assembly according to claim 1, wherein said ring is radially and outwardly expandable from a rest position, in which said one inner projection defines a first internal diameter Dr of said ring, and a stressed position, in which said one inner projection defines a second internal diameter Ds of said ring, Ds being greater than Dr, said ring being in its stressed position when said at least one inner projection cooperates with the outer surface of said coupling portion, so as to prevent rotational and translational movement of said adaptor with respect to said distal tip.

8. The assembly according to claim 7, wherein Dr ranges from 90% to 97% of the external diameter of said outer surface of said coupling portion.

9. The assembly according to claim 1, further comprising a proximal portion located proximally from said coupling portion and defining a step at a junction of said coupling portion with said proximal portion, wherein said at least one inner projection is provided on its inner surface with at least one bump, said bump being intended to cooperate with said step so as to prevent distal movement of the adaptor when said adaptor is fitted on said distal tip.

10. The assembly according to claim 1, wherein said distal tip is glass and said adaptor is plastic having a heat deflection temperature higher than 1250° C.

11. The assembly according to claim 10, wherein said plastic is polycarbonate.

* * * * *